(12) United States Patent
Howlett et al.

(10) Patent No.: US 6,960,191 B2
(45) Date of Patent: Nov. 1, 2005

(54) OVER-THE-NEEDLE SAFETY MIDLINE CATHETER

(75) Inventors: Michael Wallace Howlett, Salt Lake City, UT (US); James Victor Mercer, West Jordan, UT (US)

(73) Assignee: Infusion Advancements, LLC, Salt Lake City, UT (US)

( * ) Notice: Subject to any disclaimer, the term of this patent is extended or adjusted under 35 U.S.C. 154(b) by 78 days.

(21) Appl. No.: 10/439,435

(22) Filed: May 15, 2003

(65) Prior Publication Data

US 2004/0111059 A1 Jun. 10, 2004

Related U.S. Application Data

(60) Provisional application No. 60/432,136, filed on Dec. 10, 2002.

(51) Int. Cl.[7] .............................................. A61M 5/178
(52) U.S. Cl. .............................. 604/164.13; 604/168.01
(58) Field of Search ............................ 604/523, 164.01, 604/164.04, 164.06, 164.07, 164.08, 164.11, 164.13, 165.02, 165.03, 170.01, 171, 110, 177, 170.03

(56) References Cited

U.S. PATENT DOCUMENTS

| | | | |
|---|---|---|---|
| 3,589,368 A | * | 6/1971 | Jackson et al. ............. 604/541 |
| 4,728,322 A | | 3/1988 | Walker et al. |
| 4,773,901 A | | 9/1988 | Norton |
| 4,840,613 A | | 6/1989 | Balbierz |
| 4,840,622 A | * | 6/1989 | Hardy ........................ 604/264 |
| 4,846,812 A | | 7/1989 | Walker |
| 4,850,960 A | | 7/1989 | Grayzel |
| 4,955,863 A | | 9/1990 | Walker et al. |
| 5,195,974 A | | 3/1993 | Hardy |
| 5,683,370 A | | 11/1997 | Luther et al. |
| 5,814,021 A | | 9/1998 | Balbierz |
| 5,885,251 A | | 3/1999 | Luther |
| 6,030,369 A | * | 2/2000 | Engelson et al. ........... 604/264 |
| 6,332,874 B1 | | 12/2001 | Eliasen et al. |
| 2002/0026154 A1 | | 2/2002 | Chang |

* cited by examiner

*Primary Examiner*—Kevin C. Simmons
(74) *Attorney, Agent, or Firm*—Gale H. Thorne (57) ABSTRACT

A safety, over-the-needle midline catheter, designed generally for insertion distal to the antecubital crease to be threaded proximally to a site just distal to the axilla. An accompanying safety apparatus is employed which permits only proximal displacement of an associated needle cannula into a safety housing. The catheter has an internal lumen of constant diameter and a proximally disposed taper which in conjunction with the constant internal diameter, provides a wall thickness which effectively resists kinking and associated closure of said lumen which might result from bending of an elbow when a portion of the catheter is disposed at the cubital crease. A butterfly is disclosed which has a collet having a superiorly disposed slit and lips associated with the slit which are sufficiently thin and supple to permit the catheter to be separated from the collet (and butterfly) while wings of the butterfly are disposed upon skin of a patient. Apparatus and methods are disclosed for assisting threading the catheter through difficult anatomical pathways.

23 Claims, 10 Drawing Sheets

OVER-THE-NEEDLE SAFETY MIDLINE CATHETER

CROSS-REFERENCE TO RELATED APPLICATION

This patent application claims priority to U.S. Provisional Patent application, titled OVER-THE-NEEDLE MIDLINE CATHETER WITH RETAINING MEANS, Ser. No. 60/432,136, filed in the U.S. Patent and Trademark Office on Dec. 10, 2002 by Michael W. Howlett and James V. Mercer (Attorney's docket number 15791.1), the entire contents of this disclosure being hereby incorporated by reference herein.

FIELD OF INVENTION

This invention relates generally to vascular access and more particularly to midline catheters which are generally inserted distal to the antecubital crease and threaded proximally to a site just distal to the axilla.

BACKGROUND AND REVIEW OF RELATED ART

According to *Medical Data International*, one hundred and seventy million peripheral intravenous catheters (PIV) are expected to be sold in the United States in 2002. PIV catheters range up to three inches (7.5 centimeters) in length and typically remain in place or "dwell" from a few hours to four days according to U.S. Centers for Disease Control (CDC) recommendations. For longer therapies, PIVs are serially replaced or an extended use (extended dwell) IV catheter is inserted. The most popular extended dwell IV catheter is the peripherally inserted central catheter (PICC) that is typically sixteen to twenty four inches (forty to sixty centimeters) in length. The end or tip or the catheter is generally positioned in the superior vena cava, one to three centimeters above the right atrium of the heart. PICC insertions require a highly skilled nurse or physician for insertion as they may employ a variety of special components including a complicated, large-gauge, peel-away introducer and/or fine-gauge wires that are inserted into the vein. Local anesthesia with Lidocaine® is almost always required prior to insertion to make the procedure tolerable. In pediatrics, IV conscious sedation is frequently utilized, making the procedure less traumatic for children and their families.

Multiple complications can arise from the placement of a PICC line ranging from simple bruising to significant tissue damage, In all cases, a post-procedural chest X-Ray is used to indicate whether or not the catheter is appropriately positioned in the superior vena cava. Sometimes, the catheter tip is found to reside either in the jugular vein, in the right atrium of the heart, or malpositioned elsewhere. In the event of improper catheter tip placement, the PICC must be manipulated into proper position, removed or pulled back into a sub-optimal, non-central position. Repositioning of a PICC line can be both difficult and costly, as it often requires the use of a Fluoroscope for X-Ray imaging guidance. Failure to reposition a poorly placed catheter tip can result in complications such as abnormal heart rhythms, vessel damage, or, rarely, a perforation of the superior vena cava or other central vessels. Due to both the invasive nature of a PICC and the risks involved, a physician must provide a written order for this procedure to be performed. Many physicians are hesitant to order a PICC line for these same reasons.

In between the PIV and PICC is a mid-length (midline) catheter which is approximately eight inches (twenty centimeters) long and designed for a moderate extended dwell period of between six and thirty days. Medical Data International estimated that about three hundred and forty thousand midline catheters would be sold in the United States in 2002. It is likely that half again as many midlines are inserted each year by cutting or trimming PICCs to the midline length.

All currently known contemporary commercial midline catheters are introduced through a needle, through an introducer or over a wire. Needle diameter sizes used for midline catheter introduction are relatively large, generally ranging from 22 to 16 gauge. Introducers may have "peel-away" features for facilely disengaging such introducers following catheter introduction. In some cases, a stylet may be used in catheter placement.

In the 1990's, a midline catheter, named the Landmark manufactured by Menlo Care, Inc., was made of an elastomeric hydrogel which expanded one or two gauge sizes after insertion due to water and body fluid absorption. This catheter is no longer commercially available as it was pulled from the market following suspected adverse patient reactions to the elastomeric hydrogel.

A catheter having general vascular application is disclosed in U.S. Pat. No. 5,885,251 issued Mar. 23, 1999 to Ronald B. Luther (Luther). Luther teaches a vascular/venous access device having an insertion needle cannula disposed through the wall of a catheter and outward from the central bore of the catheter to act as an over the needle introducer. Once the catheter is introduced into a patient's vascular system, the needle is withdrawn through the wall. As well, a gripper which is used to selectively hold the catheter cannula and facilitate needle and catheter insertion is taught by Luther. The gripper has a pair of wings and a centrally disposed collet which is sized to slide along a catheter, but to seize the catheter when the wings are upwardly bent. Further, the collet is split forming a gap extending along the length of the collet. The gripper is made from a resilient polymer which permits the upward bending and removal of the gripper from the catheter by bending the wings away from the gap, thereby expanding the gap to free the gripper from the catheter. There is no needle safety procedure which affords protection from a contaminated needle removed from a catheter found in Luther.

U.S. Pat. No. 4,840,613 issued Jun. 20, 1989 to Daniel J. Balbierz (Balbierz) discloses a catheter assembly including a cannula with an over-the-needle insertion, a slitted sheath which affords a protective sterile field proximal from a gripped insertion member and an insertion needle which is retracted by a wire. U.S. Pat. No. 5,195,974 issued Mar. 23, 1993 to Dwayne E. Hardy (Hardy) discloses a safety wire needle extractor construction which retracts a longitudinal piercing member (needle) into entrapment in a receiving tube. The needle is trapped in the tube by pulling a wire through a proximal orifice which is smaller in diameter than the needle and the wire and needle through a distal orifice which is formed to reduce likelihood of any further distal displacement of the needle.

Midline catheters may be inserted through the cephalic, basilic or median cubital veins, although most technicians consider the basilic vein to be optimal. Some technicians prefer that the point of insertion be just above the antecubital space to minimize mechanical (kinking) problems associated with arm bending at the elbow. However, inserting and servicing a catheter at such an insertion point is considered to be less desirable than just below the antecubital space.

Of course, sterile technique is essential and a sterile field must be maintained during catheter placement. In some cases, fluoroscopic imaging is required to place a catheter due to physiological vasculature abnormalities.

As midline catheters are intended for extended use (e.g. up to 30 days), phlebitis is a concern. Catheter parameters, such as catheter diameter and biological inertness, pliancy, and suppleness of catheter material are considerations which affect midline catheter design relative to phlebitis considerations.

BRIEF SUMMARY AND OBJECTS OF THE INVENTION

This novel invention provides an innovative safety midline catheter which permits over-the-needle catheter insertion, and, therefore, use of standardized insertion techniques currently employed for insertion of other catheters (e.g. PIV catheters). Designed to be able to be inserted below the antecubital crease, the catheter of the present invention is mildly tapered and thickened proximally (near the catheter hub), to compensate for bending of an elbow which would otherwise challenge patency of the catheter, while retaining a lumen of constant size throughout its length. This novel midline catheter has a tip, of sufficiently high durometer to facilitate over-the-needle insertion, proximally affixed to a body of lesser durometer to provide necessary flaccidity and pliability of the major portion of the catheter for use in a medium dwell period catheter. The mild taper not only provides protection against kinking, but also improves closure at the site of catheter insertion, thus reducing bleeding from the insertion site.

The catheter is preferably an extruded synthetic resinous material which is selectively filled with a radiopaque substance such that a linear window along the length of the catheter is provided for blood flash visualization. A series of readily visible surface marks are also distributed along the catheter at regular intervals for facile determination of inserted catheter length.

A displaceable butterfly is disposed to be displaced along the length of the catheter generally to facilitate catheter insertion, although the butterfly may also be selectively used to anchor a partially inserted catheter. The butterfly has a normally superiorly disposed collet through which the catheter is threaded and which permits displacement of the butterfly relative to the catheter. A pair of wings disposed along each side of the collet have raised ridges which securely grasp the collet (and catheter disposed therein) when folded together. The collet has a superiorly disposed medial slit along its length which forms a pair of lips which are sufficiently flaccid to be opened by outwardly directed pressure from inside the collet. Thus, the catheter may be extricated from the collet by upwardly lifting a proximal portion of the catheter through the lips, leaving the butterfly free for disposal. Also, the lips are facilely parted to permit distal progress of the tapered portion of the catheter into and through the collet.

A hollow medical needle having a sharpened distal tip is exposed from within the distal end of the catheter. Proximally, the needle is securely affixed to a flexible wire which is threaded through the catheter lumen and used to extract the needle from the catheter. The wire is used to withdraw the needle into a safety housing upon venipuncture, but prior to complete catheter insertion into a vessel of a living being. As any distal movement of the needle relative to the catheter may yield an unsafe condition (e.g. catheter perforation) once the needle tip is withdrawn into the lumen of the catheter, wire movement is restricted to displacement away from venipuncture site (i.e. proximal displacement) relative to the long axis of the catheter. On a proximal end, the wire is affixed to a cap which is releasibly affixed to the safety housing to assure controlled extraction of the needle.

Accordingly, it is a primary object to provide a safety needle midline catheter system which may be effectively inserted and retained below the antecubital crease for midline catheter use.

It is another primary object to provide an over-the-needle midline catheter which, when inserted below the antecubital crease in the arm of a patient, retains patency when an associated elbow of the patient is bent to close the crease.

It is a fundamental object to provide for needle retraction into a safety housing following venipuncture.

It is another fundamental object to provide a needle retraction mechanism which assures all needle displacement relative to the catheter is restricted to a proximal direction.

It is an object to provide a secure, but facilely releasible lock which assures no displacement of the needle until the lock is manually unfastened preparatory to retracting the needle.

It is an object to provide a window which extends along the catheter whereby a blood flash signaling entry into a blood vessel may be seen.

It is an object to provide a liquid flow barrier proximal to the catheter such that blood flow is restricted to catheter pathways which are distal to the safety housing into which the needle is retracted.

It is an object to provide a liquid flow barrier which permits venting air from the catheter to permit proximal blood flow within the catheter.

It is an object to provide an elongated radiopaque strip along the wall of the catheter which permits fluoroscopic tracking of a pathway of an inserted catheter.

It is an object to provide circumferential marks about the catheter spaced at predetermined intervals for the purpose of determining distance a catheter is inserted.

It is an important object to provide an associated butterfly member by which the catheter is gripped for purposes of inserting both needle and catheter and otherwise for maintaining position control of the catheter during use, the butterfly being displaceable along the catheter, having a slit collet disposed about the catheter and being formed of material which is sufficiently flexible to permit opening of the slit in the collet to permit disengagement of the catheter from the collet of the butterfly while the butterfly is resident upon a skin surface of a patient.

It is another important object to provide a catheter which has a distal over-the-needle, nose section which has a first outside diameter and which has sufficient rigidity for over-the-needle insertion.

It is also another important object to provide a catheter of which there is a portion which is proximal to the distal nose section, which is more supple than the nose section, but which has sufficient rigidity for threading the nose section to a target site just distal from the axilla and which has a first outer diameter which is the same outer diameter of the nose section.

It is yet another important object to provide a catheter which is proximally tapered, from the first outer diameter to a second larger outer diameter.

It is an object to provide the taper at a site along the catheter such that the smaller diameter potion of an inserted catheter is displaced beyond the antecubital crease and the taper and larger diameter portion are ordinarily disposed in the region of the antecubital crease.

It is a significant object to provide a catheter having a substantially constant internal lumen along the length of the catheter such that the tapered region and the region of the second diameter has an increased wall thickness which effectively resists kinking and other closure of the catheter lumen to retain patency thereof.

It is an object to provide a tapered catheter which has a thickened wall at the venipuncture site which effectively increases resistance to antiseptic (e.g. alcohol) degradation and gently plugs the insertion site to reduce bleeding.

It is an object to provide secondary methods and apparatus which aid threading a catheter into a desired, predetermined site.

It is an object to provide a distal nose section of a catheter which is bulged to mildly dilate tissue at the insertion site to reduce friction thereat.

These and other objects and features of the present invention will be apparent from the detailed description taken with reference to accompanying drawings.

DETAILED DESCRIPTION OF THE ILLUSTRATED EMBODIMENTS

In this description, the term proximal is used to indicate the segment of a device or a part of a device which is normally closest to a technician using the device. The term distal refers to the other end. Reference is now made to the embodiments illustrated in FIGS. 1–23 wherein like numerals are used to designate like parts throughout. Numbers with primes are used to depict either similar parts or related parts of the same base number.

Figure 1:
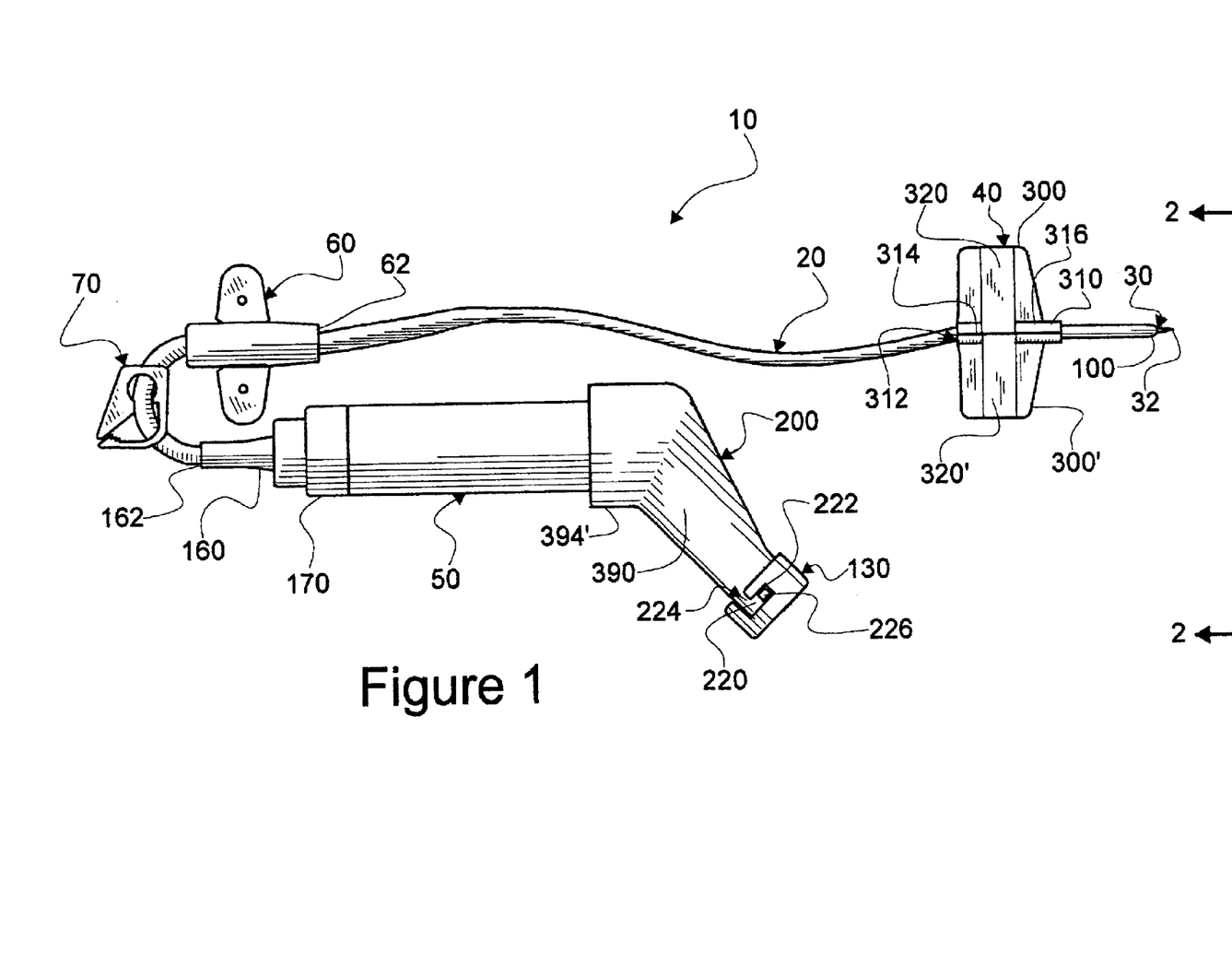
FIG. 1 is top elevation of a horizontally disposed over-the-needle, safety midline catheter system according to the present invention, the system comprising a needle cannula, a midline catheter and a displaceable butterfly for gripping the needle cannula and catheter during insertion procedures.

A safety midline catheter system 10 made according to the instant invention is seen in FIG. 1. System 10 generally includes a midline catheter 20, an insertion needle cannula 30 having a sharpened tip 32, a butterfly 40 used for gripping catheter 20 and cannula 30 during catheter insertion and a needle safety housing 50. Note that catheter 20 resides about cannula 30 for the purpose of over-the-needle insertion. Also seen in FIG. 1, is a catheter stabilization component 60 and a snap closure, catheter occluding ring 70, both of which are commonly used and well known in catheter art. Reference is made to a distal lip 62 of component 60, form and function of which is disclosed hereafter.

Figure 2:
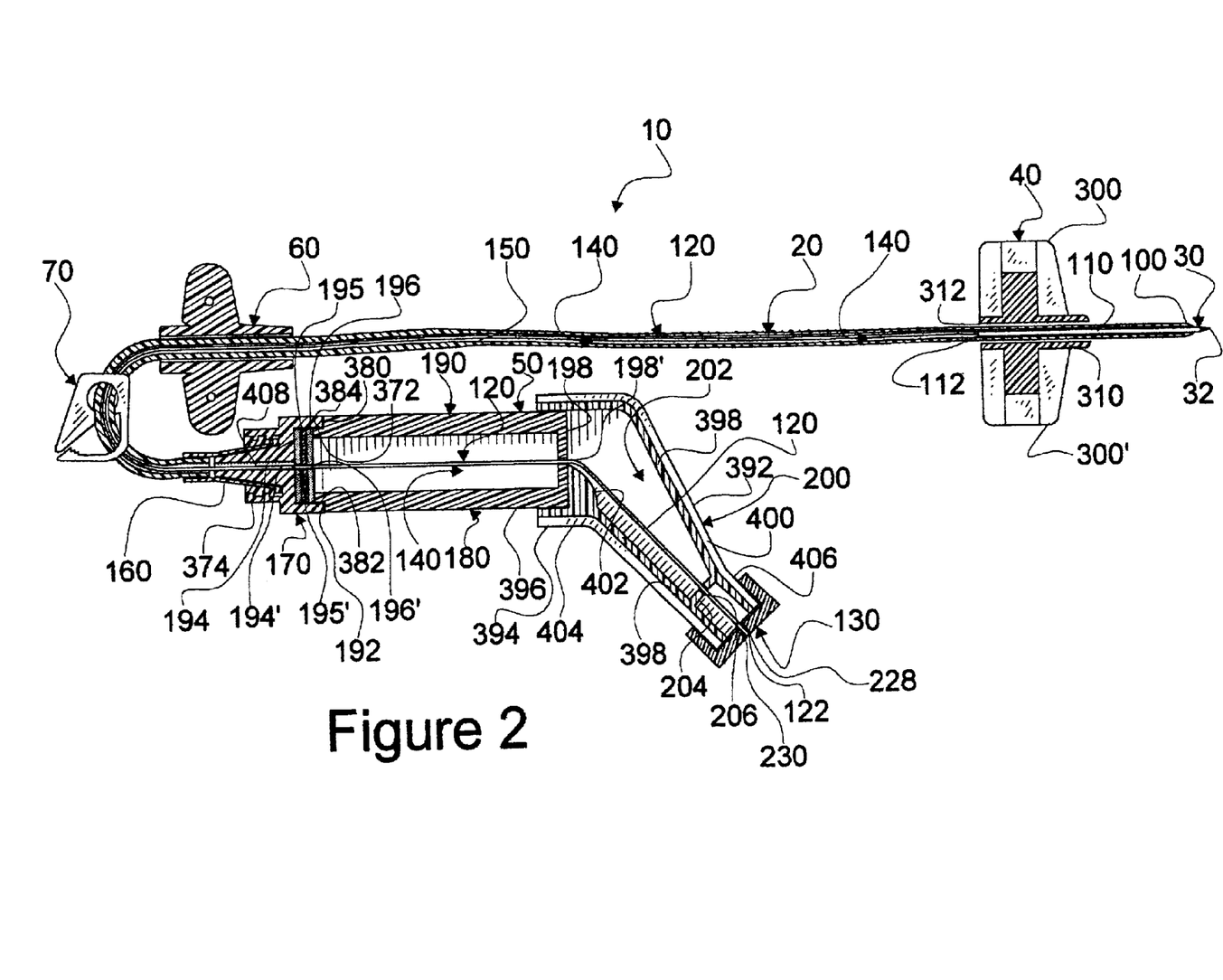
FIG. 2 is a medial section of the safety midline catheter system taken along lines 2—2 in FIG. 1.

Needle cannula 30 is better seen in FIG. 2. Tip 32 is clearly seen to extend distally from catheter 20. Note that catheter 20 is "necked down" about cannula 30 a its most distal end 100 to facilitate entry at a penetration site. Needle cannula 30 has an elongated body 110 which has sufficient length to be securely gripped by pressure imposed via butterfly 40. At a proximal end 112 of cannula 30, body 110 is securely affixed to a thin wire 120 which is employed to retract needle cannula 30 after catheter 20 is satisfactorily disposed in a vessel. On a proximal end 122, wire 120 is firmly affixed to a cap 130. Cap 130 is designed to be a handle which facilitates displacement of wire 120.

As is well known in over-the-needle catheter art, it is not advisable, and, in fact, may be considered poor medical practice, to attempt to refeed a needle cannula distally once needle retraction has been initiated. For this reason, system 10 does not permit distal displacement of cannula 30 relative to catheter 20. As seen in FIG. 2, wire 120 is threaded along a path 140 which proceeds through an internal lumen 150 of catheter 20, a female luer fitting 160, a male luer-lock fitting 170, which is affixed to an elongated, mostly closed vessel 180 to form a distal portion 190 of safety housing 50.

Vessel 180 is closed at a distal end 192 by three pads, numbered 194, 195 and 196, except for holes, 194', 195' and 196', which elastically close about, but permit passage of wire 120. Similarly, on a proximal end 198, vessel 180 has a small hole 198' which is sized to permit passage of wire 120, but too small to pass needle cannula 30.

Proximally affixed to vessel 180 is another hollow elongated, but angled vessel 200 which defines an angular pathway 202 for wire 120 as wire 120 is pulled through hole 198' by proximal displacement of cap 130. Also, distal to cap 130, vessel 200 has a partially closed structure 204 which has a medially disposed slot 206 which restricts transverse motion of wire 120 when displaced distally. Note that slot 206 becomes a hole when vessel 200 is fully assembled.

Figure 3:
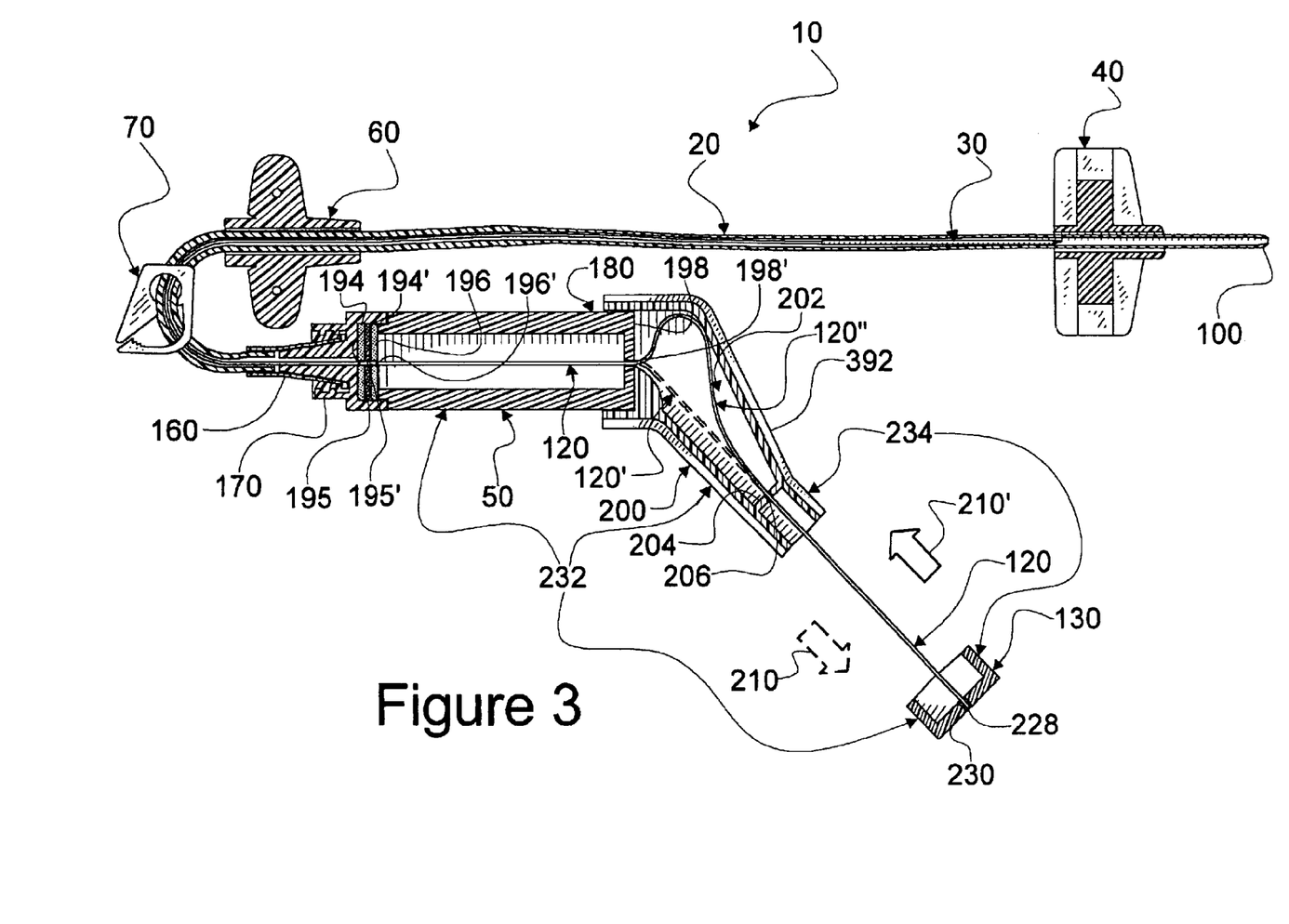
FIG. 3 is a is a medial section, similar to the section of FIG. 2, but with a needle cannula used for inserting the midline catheter partially retracted.
Figure 4:
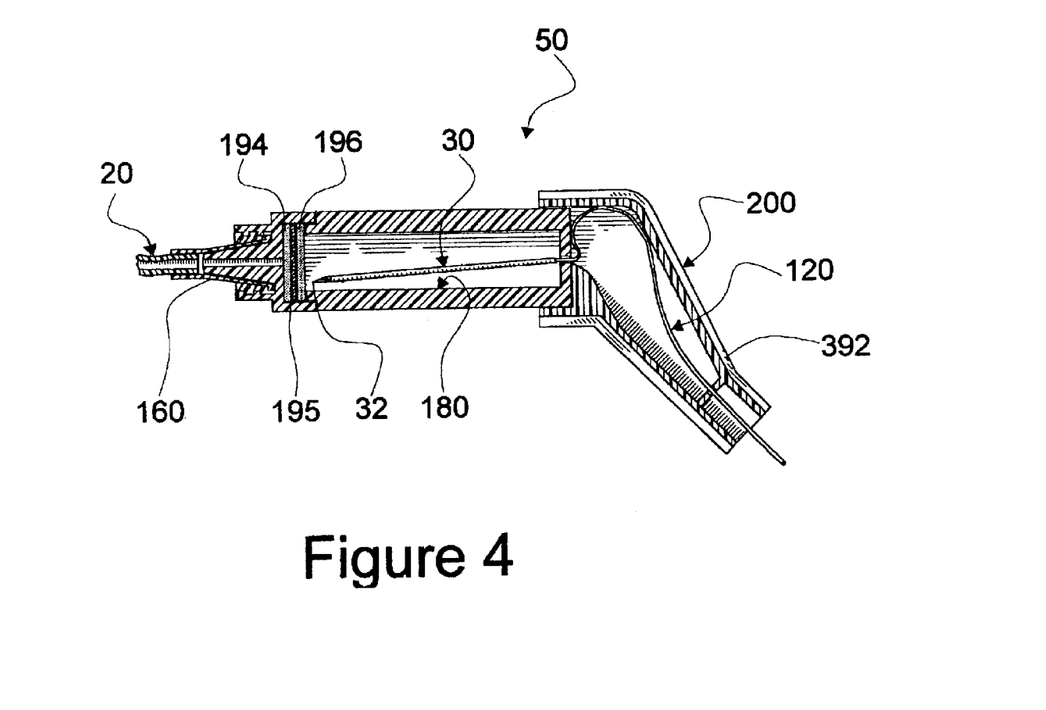
FIG. 4 is a portion of the catheter system seen in FIG. 3 with the needle cannula fully retracted into a needle safety housing.

Reference is now made to FIGS. 3 and 4 wherein a reaction to bi-directional application of force to displace wire 120 is seen. As seen in FIG. 3, when wire 120 is displaced proximally in the direction of arrow 210 (drawn with dashed lines), wire 120 is in tension and follows a substantially straight path through slot 206 as shown by a dashed line portion 120' of wire 120. However, when an attempt is made to displace wire 120 distally in the direction of arrow 210', wire 120 proceeds along a diverse angulated pathway toward hole 198' thereby securely resisting distal movement of wire 120 through hole 198' resulting in a distortion of wire 120 into a misdirected arch, such as arch 120", which negates further distal travel of wire 120. While such geometric constraints may be used to effectively retard wire 120 from being distally displaced beyond hole 198', other methods within the scope of the instant invention, such as use of unidirectional brakes and clutches, for example, may also be used.

This method of restricting distal travel of wire 120 is also usefully applied when needle cannula 30 is finally displaced proximally into vessel 180. Note that as wire 120 and attached needle cannula 30 are displaced proximally, both are wiped in combination by pads 194, 195 and 196. Also, in combination, pads 194, 195 and 196 are sufficiently elastic and pliable to close any fluid pathway afforded by a combination of holes 194', 195' and 196' as either wire 120 or needle cannula 30 is displaced therein or when needle cannula 30 has been completely pulled therethrough. A more detailed disclosure concerning pads 194, 195 and 196 is provided hereafter.

Finally, proximal displacement of needle cannula 30 is limited by a diameter of hole 198' which is sized to permit facile transport of wire 120, but which is smaller than the axial diameter of needle cannula 30. It is important to note that, due to impediment to distal displacement of wire 120 afforded by interaction of hole 198' and angulation of pathway 202 in vessel 200, no additional impediment to restrict further distal travel of needle cannula 30 need be provided. Once needle cannula 30 is disposed in vessel 180 as seen in FIG. 4, it is effectively trapped therein. Restriction of distal displacement of needle cannula 30 assures secure, safety containment of needle cannula 30 and sharpened tip 32 within vessel 180.

As distal displacement of needle cannula 30 is fully impeded, it is important that any inadvertent proximal displacement of needle cannula 30 be avoided. As seen in FIG. 1, cap 130 has an angled retention slot 220 having a transverse length 222 for latching and an associated opening 224, similar to a bayonet lock. Vessel 200 has a raised key 226, sized to slide within slot 220 and to releasibly separate from cap 130 via opening 224. Thus, cap 130 is affixed to vessel 200 until cap 130 is rotated until key 226 is aligned with opening 224 and displaced proximally to initiate proximal displacement of wire 120 and needle cannula 30. It is preferred that cap 130 be freed from attachment to vessel 200 by about a quarter turn of cap 130 relative to vessel 200.

Cap 130 is seen displaced from vessel 200 in FIG. 3. Also, as seen in FIG. 3, wire 120 is firmly affixed to cap 130. While other methods of affixing wire 120 to cap 130 may be used withing the scope of the invention, in this embodiment, wire 120 is securely affixed to cap 130 via a hole 228 and there affixed with adhesives 230. A safety needle enclosure apparatus 232 is formed by a combination of vessel 180, vessel 200 and cap 130. (See FIGS. 3 and 4.) Cap 130 is releasibly affixed to vessel 200 and securely attached to wire 120 to securely affix wire 120 in place until separated from vessel 200 for the purpose of retrieving needle cannula 30 proximally and ultimately into safety of vessel 180 (see FIG. 4). Also, cap 130, when removed from vessel 200, may be displaced proximally and distally, but wire 120 can only be displaced proximally within vessel 180. Thus, in combination, vessel 200 and cap 130 (affixed to wire 120) provide a means 234 for securely, but releasibly affixing wire 120 in place, for proximally displacing wire 120 (and therefore) needle cannula 30 and for effectively resisting distal displacement of wire 120.

Figure 6:
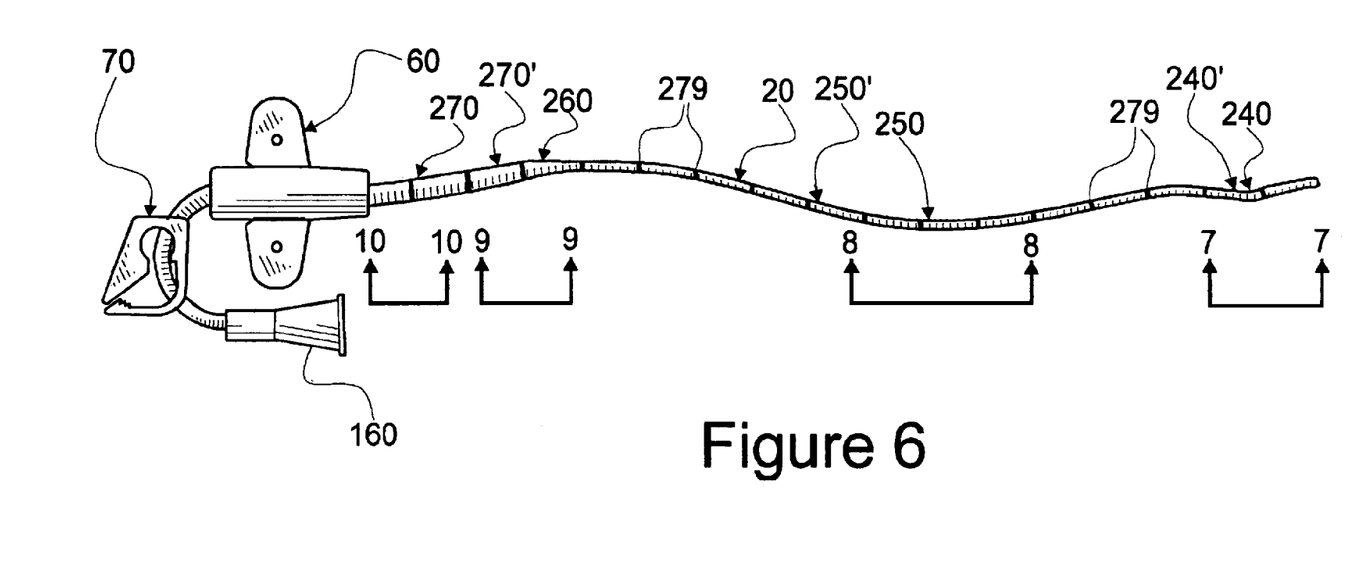
FIG. 6 is a top elevation of a midline catheter according to the present invention.

Catheter 20 with needle cannula 30, wire 120 and safety housing 50 removed is seen in FIG. 6. Catheter 20 may be envisioned as having three distinctive sections, a distal tip section 240, an elongated section 250 of constant diameter contiguous with distal tip, a tapered section 260 wherein the outer diameter of catheter 20 is enlarged from the outer diameter of elongated section 250 to a constant enlarged outer diameter of a section 270. Individual magnified examples of each of these sections are seen in FIGS. 7–10.

Figure 7:
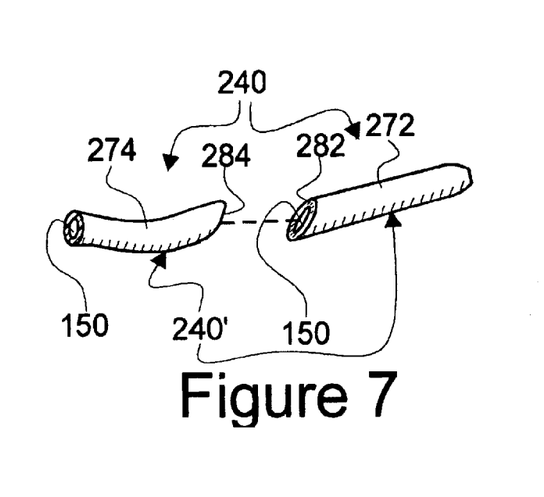
FIG. 7 is a section, of the catheter seen in FIG. 6, taken between arrows 7—7.
Figures 8, 10:
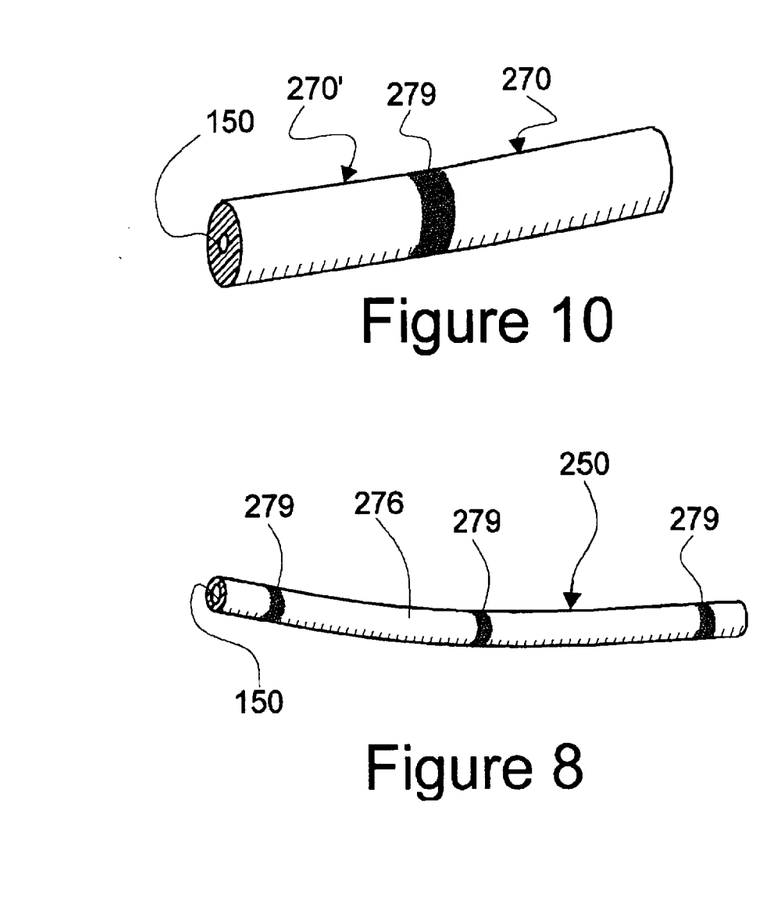
FIG. 8 is a section, of the catheter seen in FIG. 6, taken between arrows 8—8.
FIG. 10 is a section, of the catheter seen in FIG. 6, taken between arrows 10—10.
Figure 9:
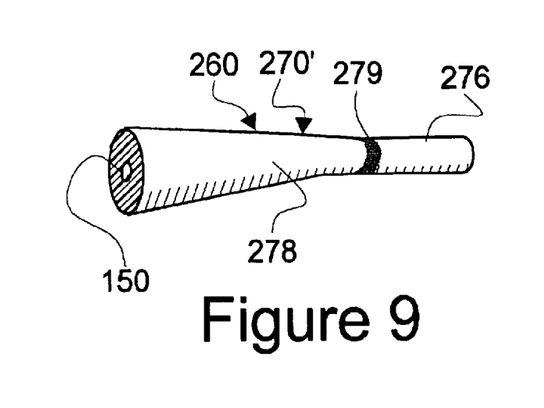
FIG. 9 is a section, of the catheter seen in FIG. 6, taken between arrows 9—9.
Figure 11:
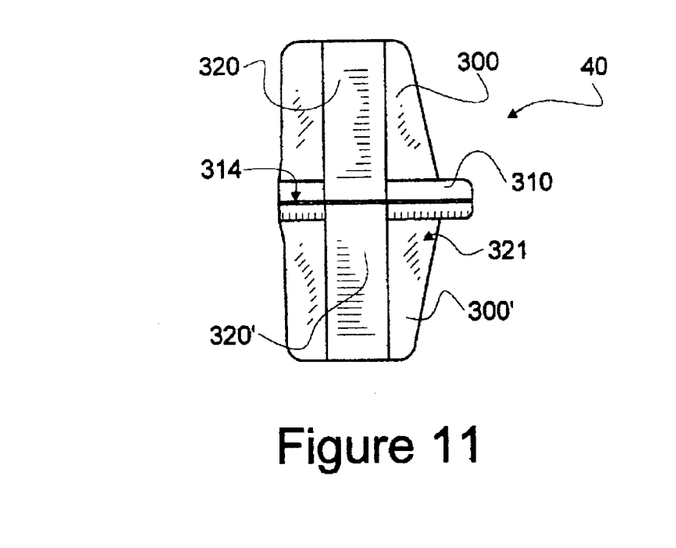
FIG. 11 is a solitary, but magnified, butterfly disposed as seen in FIG. 1.
Figure 12:
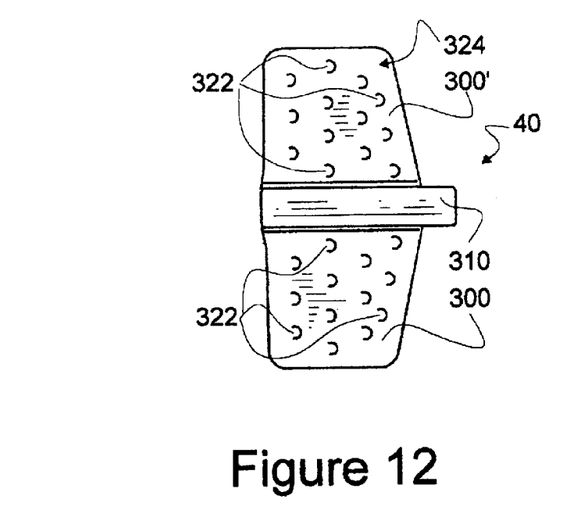
FIG. 12 is a bottom elevation of the butterfly seen in FIG. 11.
Figure 13:
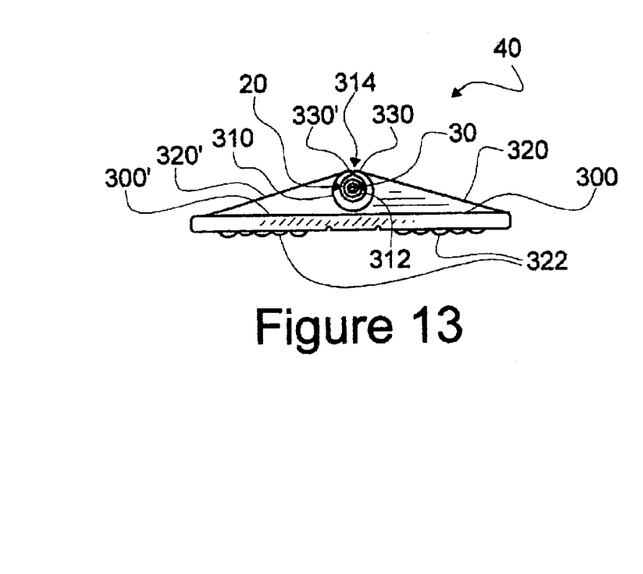
FIG. 13 is a frontal elevation of the butterfly seen in FIG. 11 with a catheter and needle cannula disposed therein.
Figure 14:
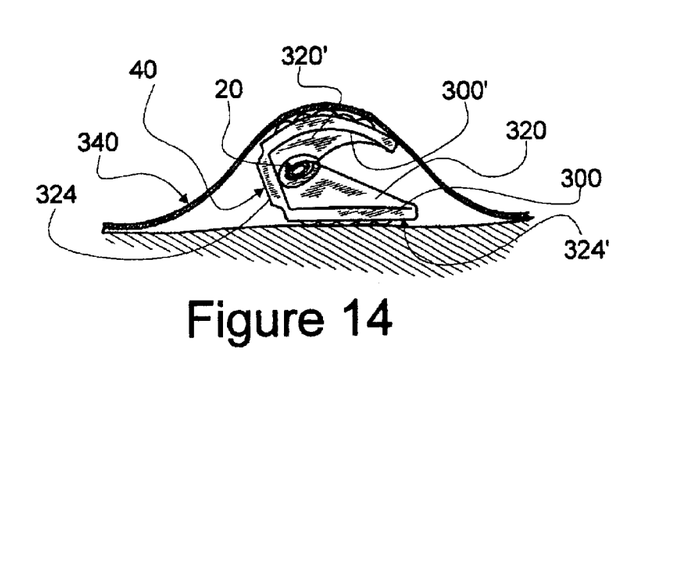
FIG. 14 is another configuration of the butterfly seen in FIG. 11 folded and anchored by a bandage to secure a catheter disposed in a collet thereof.

As seen in FIG. 7, distal tip section 240 may be considered as being made in two portions, a most distal portion 272 and a more proximal portion 274. Portions 272 and 274 are preferably fabricated from two different materials or, at least, materials of two different durometers, a higher durometer (for stiffness) being used in the most distal portion 272. FIG. 8 shows section 250 which represents a portion 276 of catheter 20 which is constant in outside diameter and of the same outside diameter as portion 274 and which is disposed between portion 274 and section 260. Seen in FIG. 9 is section 260 which has a tapered portion 278, tapered from the outer diameter of portion 276 to an outer diameter of enlarged diameter section 270, which is seen in FIG. 10. For a more inclusive definition, catheter 20 may be considered to comprise a distal section 240', a medial section 250' and a proximal section 270'. Distal section 240' comprises distal section 240, seen in FIGS. 6 and 7. Proximal section 270' comprises sections 260 and 270 seen in FIGS. 6, 9 and 10. Medial Section 250' comprises the elongated portion of catheter 20 which lies between distal section 240' and proximal section 270'.

A design may be varied in many ways within the scope of the present invention, however, it is presently preferred that material selected for manufacture of catheter 20 be Carbothane®, currently available from Thermedics Polymer Products. Carbothane® is an aliphatic, polycarbonate base TPU that is available over a wide range of durometers, colors and radioipacificers. It has excellent oxidative stability and long-term biostability and is immune to alcohol degradation. Carbothane® products may be formed by extrusion and may be variably extruded and insert molded. Details of materials which may be selectively used in catheter 20 are provided hereafter.

As well, it is preferred that catheter 20 have two different visual characteristics distributed along its length. A major portion of the catheter should be relatively clear and translucent, permitting blood flash to be readily seen along the full length of catheter 20; however, it is also preferred that catheter 20 be "fluoroscopically trackable" and therefor should have a line of radio-opaque material distributed linearly along the length thereof.

Proximal to portion 274 is an elongated portion 276 of constant diameter, which is seen by example in section 250 in FIG. 8. Portion 276, having a constant internal and outside diameter, is disposed between portion 274 and a tapered portion 278 seen as a part of tapered section 260 in FIG. 9. Tapered portion 260 increases the outside diameter of catheter 20 proximally until it reaches a constant outside diameter as seen in section 270 in FIG. 10. As seen in FIGS. 7 and 8–10, catheter 20 also has readily visible equally spaced markings, generally numbered 279, (preferably one centimeter apart) as indicators for determining catheter 20 insertion distance. Further, as seen in FIGS. 7–10, catheter 20 is longitudinally traversed throughout its entire length by a constant diameter lumen 150. The constant diameter of lumen 150 in combination with increasing diameter of catheter 20 in tapered portion 278 and section 270 provides a region across a proximal portion of catheter 20 which resists kinking and resulting loss of patency of lumen 150. This is particularly useful when catheter 20 is inserted distal to the antecubital crease for the purpose of being threaded proximally to a site just distal to the axilla. In such a case, occlusion due to bending of an elbow is significantly reduced by increased thickness of the catheter in the region of the bent elbow. At its most proximal end, catheter 20 is securely affixed to a female luer fitting, numbered 160 (see FIGS. 1–3). Fitting 160 has a distal lip interface 162, the form and function of which is disclosed hereafter.

Other appurtenances, which may be affixed to catheter 20, are catheter stabilization component 60 and a snap closure, catheter occluding clamp 70, as seen in FIG. 6. Component 60 is like catheter tie down components which are commonly use for long term stabilization of catheters. Note that distal lip 62 of component 60 (see FIG. 1) should be configured to be sufficiently obtuse to preclude entry into an insertion site. Also, to provide for a circumstance where component 60 and occluding clamp 70 are removed from catheter 20, lip interface 162 should also be sufficiently obtuse to preclude entry into an insertion site. Similarly occluding clamp 70 is a device commonly used to control fluid (often blood) flow through catheter (in this case, by occluding lumen 150). Occluding clamps, of which clamp 70 is an example, are currently available commercially.

Catheter 20 may be fabricated as follows. Distal portion 272 may be formed by insert molding of two Carbothane® materials, PC-3555D and PC-3555D-B20. Both PC-3555D and PC-3555D-B20 have a shore hardness of 60 D. PC-3555D is clear while PC-3555D-B20 has a barium content of 20% for radio-opacity and an added green dye for color. PC-3555D-B20 is molded with PC-3555D to provide a radiopaque strip approximately one millimeter wide along the length of portion 272. As an example, distal portion 272 may be two centimeters in length.

The rest of catheter is preferably formed by controlled extrusion of two other Carbothane® materials, PC3585A and PC3585A-B20, both of which have a shore hardness of 84A. PC3585A-B20 has a barium content of 20% for radio-opacity and has an added green dye. PC3585A-B20 is extruded simultaneously with PC3585A to form a mostly clear catheter 20 having an elongated radiopaque line of about one millimeter in width along the length thereof.

As seen in FIG. 7, portions 272 and 274 have complimentary faces 282 and 284, respectively, at which portion 272 is joined to portion 274. Preferably, each face 282 and 284 is formed by an angular cut of 45° off the medial axis of lumen 150. Portion 272 preferably is affixed to portion 274 by adhesion. Adhesives for such are well known in use of Carbothane® materials, produce a bond which is at least as strong as the Carbothane® material and will, therefore, not be treated further herein.

As examples, lumen 150 may range from 0.028 (0.070 centimeters) to 0.035 inches (0.090 centimeters or the size of 20 Gauge per the Stubbs Needle Gauge System) in diameter. External diameter of portion 276 may be about 0.044 inches (0.112 centimeters or the size of 19 Gauge per the Stubbs Needle Gauge System). Tapered portion 278 increases outside diameter of section 270 to 0.049 inches (0.124 centimeters or the size of 18 Gauge of the Stubbs Needle Gauge System). Catheter 20 may be 20 to 22 centimeters in length. For a catheter 20 having a length of 22 centimeters, portion 272 may be two centimeters in length. Portion 276, including portion 274, may be 14 centimeters in length. Portion 278 may be one centimeter in length, and section 270 may be five centimeters in length. Taper of portion 278 is preferably linear.

Also as examples, needle cannula 30 may be a 20 to 21 gauge needle made from stainless steel and teflon treated and should be sufficiently long to be securely engaged by gripping via butterfly 40 when being used in catheter insertion. Nominally, cannula 30 may be two and a half centimeters in length. Sharpened tip 32 may have a bevel which is well known in the art of making needles for over-the-needle catheter insertion. Wire 120 may be 27 gauge stainless steel and made to extend from attachment to needle cannula 30 to cap 130.

Reference is now made to FIGS. 1–3 and 12–16. An important element of the present invention is butterfly 40 which is slidably disposed about catheter 20, both of which are seen in FIG. 1. Butterfly 40, as is common with butterfly elements of some other catheters, has a pair of pliant wings 300 and 300' juxtaposed one on each lateral side thereof. As may be seen in FIG. 2, butterfly 40 has a collet 310, medially disposed between wings 300 and 300', having an elongated lumen 312 through which catheter 20 is slidably disposed. Referring again to FIG. 1, collet 310 has a superior slit 314 medially disposed along a top side 316. Further butterfly has a pair of bracing ribs 320 and 320' superiorly disposed upon respective wings 300 and 300' which are used when wings are articulated to compress catheter 20 and grip needle cannula 30 through catheter 20 when needle 30 is disposed within collet 310 and to grip catheter 20 only when needle cannula has been proximally displaced.

As seen in FIGS. 11–16, butterfly 40 is molded of a pliant synthetic resinous material to have a plurality of useful modes of utility. Such materials are commonly available in catheter construction art and will not be further treated herein. As previously cited, and seen in FIG. 11, a superior side 321 of butterfly 40 has a pair of juxtaposed bracing ribs 320 and 320' superiorly affixed to wings 300 and 300', respectively. Ribs 320 and 320' are disposed about slit 314 such that, when wings 300 and 300' are upwardly articulated, slit 314 is closed and squeezing pressure is applied against collet 310.

Inferiorly, each wing 300 and 300' has a series of bumps, generally numbered 322, on a contiguous underside 324. See FIG. 12. The bumps provide a surface for gripping butterfly 40 and therefore catheter 20 and needle cannula 30 via pressure placed upon wings 300 and 300'. Relative geometry between wings 300 and 300', ribs 320 and 320', collet 310, catheter 20 and needle cannula 30 is seen in frontal perspective in FIG. 13. Note thinning of superiorly disposed lips 330 and 330' of collet 310 at slit 314. This thinning provides an important feature and operational element for catheter system 10 and is treated more fully hereafter.

As butterfly 40 may be freely displaced along catheter 20, it is important that articulated wings 300 and 300' distort that portion of catheter 20 which is resident in collet 310 of butterfly 40 to assure catheter 20 is effectively secured thereat by butterfly 40. Such a case may be seen in FIG. 14. In this case, catheter 20 is seen in cross section with needle cannula 30 removed therefrom. Wing 300' has been articulated relative to wing 300 to distort catheter 20 for the purpose of holding catheter 20 in place. In this instance, underside 324' of wing 300 is disposed against skin of a patient and a bandage 340 is disposed about butterfly 40 to securely hold butterfly 40 and therefore catheter 20 in place.

Figure 15:
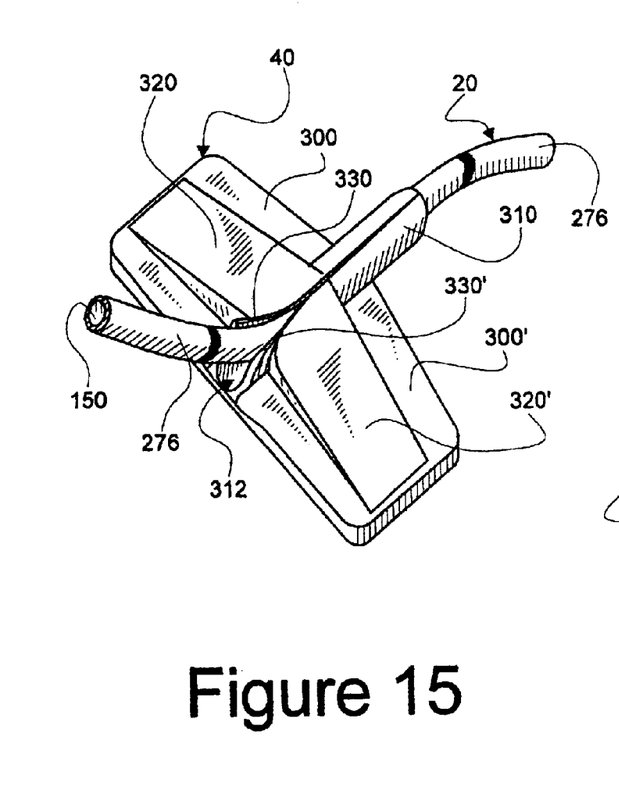
FIG. 15 is a perspective of the butterfly and catheter variously seen in FIGS. 1–3 wherein the catheter is being lifted from a slit the collet thereof which permits extricating the catheter from a planarily disposed butterfly.
Figure 16:
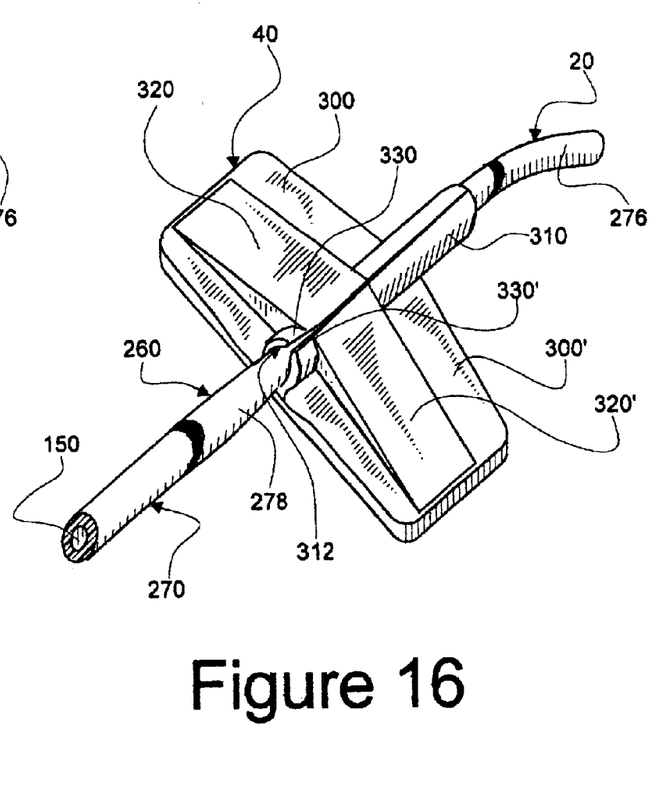
FIG. 16 is a perspective of the butterfly seen in FIG. 15 wherein taper of the catheter is seen to part lips of a slit in the collet.

Reference is now made to magnified examples of butterfly 40 and catheter 20 found in FIGS. 15 and 16 wherein lips 330 and 330' are parted by action of catheter 20. In FIG. 15, upward displacement of catheter 20 readily displaces lips 330 and 330' thereby permitting catheter 20 to be separated from butterfly 40 without articulating wings 300 and 300'. Note, in FIG. 16, that lips 330 and 330' are also parted as tapered portion 278 of section 260 enlarges effective circumference of collet 310. This parting permits use of collet 310 which has an internal diameter which is sized to closely channel portion 276 of catheter 20 as a closely sized sliding element, yet opens to permit use of butterfly 40 about portion 278 and section 270. Also, the parting permits facile displacement of catheter 20 from butterfly 40 at and more proximal to section 278.

Figure 5:
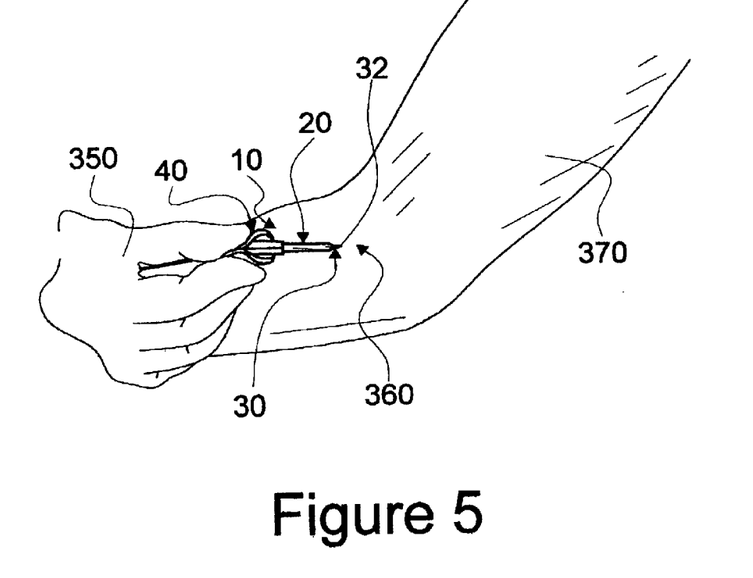
FIG. 5 is a perspective of a portion of the catheter system of FIG. 1 displaced along a patient's arm for insertion into an antecubital site.

Reference is now made to FIG. 5 wherein a gloved hand 350 of a technician is seen preparing to insert sharpened tip 32 of needle cannula 30 and subsequently catheter 20 into an exemplary penetration site 360 of a patients arm 370. Note that the site selected is in a region of arm 370 which is distal to the antecubital crease.

Assembly of midline catheter system 10 is straight forward. Attention is drawn to FIGS. 1-4. Following is an example of an assembly process for system 10. Preparatory to assembly, wire 120 is affixed to needle cannula 30. Catheter 20 is affixed to female luer fitting 160. A male luer-lock fitting 170 which has a cylindrical pocket 372 for housing a set of circular pads 194, 195 and 196 is provided. (See FIG. 2.) Pads 194 and 196 are preferably made from an open celled foam which is permeable to fluid flow. Pad 195 should be permeable to gas, but impermeable to liquids. Such a material is Gortex, which is well known in both the medical and clothing arts. Pad 195 is sandwiched between pads 194 and 196 to provide a liquid (blood) barrier for vessel 180. (See FIG. 4.) Note that when wire 120 and needle cannula 30 are drawn through pads 194, 195 and 196 each pad wipes liquids from contacted surfaces and effectively blocks proximal fluid flow. Also, note that holes 194' 195' and 196' should elastically close to block blood flow into vessel 180 once needle cannula 30 is disposed therein.

As seen in FIG. 2, fitting 170 has a luer lock portion 374 to which female fitting 160 may be securely, but releasibly affixed. Proximally, fitting 170 has a circular edge 380 and an associated hollow interior cylindrical surface 382 which provides a joint for a complimentary distal portion 384 of vessel 180. Vessel 180 is cylindrical in shape with nearly closed proximal end 198 and hole 198'. Note that both fitting 170 and vessel 180 can be made as individual integral parts by standard injection molding processes. Fitting 170 and vessel 180 may be injection molded from polystyrene or polycarbonate.

Vessel 200 is preferably made in two parts and assembled as a clam shell. One part 390 is seen, superiorly disposed, in FIG. 1. A second part 392 is seen in FIGS. 2-4. As seen in FIG. 2, part 392 is an arcuate housing which has a cylindrical, semicircular section 394 which is sized to conformably fit about an exterior surface 396 of vessel 180. (See FIG. 2.) Part 390 has a similar complimentary section 394' as seen in FIG. 1. Part 392 has a raised internally disposed edge 398 which is medially offset from a planar edge 400. (See FIG. 2.) Part 390 has complimentary edge features (not shown) which permit parts 390 and 392 to be joined and adhesively bonded to make a hollow part through which wire 120 traverses. To assure a useful control of displacement of wire 120, a guide wedge 402 is disposed at an angular site 404 of vessel 200 and structure 204 and associated slot 206 is disposed near a proximal end 406 of vessel 200. As previously cited, key 226 is disposed upon pat 390 (see FIG. 1) to be used for releasable attachment of cap 130.

Steps in system 10 assembly may be accomplished as follows: (See FIG. 2.)

1. Affix clamp 70 and component 60 to catheter 20.
2. Affix butterfly 40 to catheter 20.
3. Thread a proximal end of wire 120 with needle cannula attached through distal end 100 of catheter 20.
4. Sandwich pads 194, 195 and 196 into pocket 372 of fitting 170.
5. Thread wire 120 to luer fitting 160 and through a medial thru hole 408 of fitting 170 and through pads 194, 195 and 196.
6. Affix fitting 170 to fitting 160.
6. Thread wire 120 through along path 140 through vessel 180 and through hole 198'.
7. Securely affix vessel 180 to fitting 170.
8. Lay wire 120 along pathway 202 and through slot 206 with wire 120 extending proximally outside vessel part 392.
9. Affix part 390 to part 392 to form vessel 200 and a hole about slot 206.
10. Securely affix vessel 200 to vessel 180.
11. Thread wire 120 through hole 228 of cap 130.
12. Affix cap 130 to vessel 200.
13. Securely affix wire 120 to cap 130 in hole 228 with adhesives 230.
14. Remove excess length of wire 120.

In some vessel pathways, threading of a catheter may be more difficult than others due to anatomical anomalies. To dispose distal end 100 of catheter 20 at a desired site may require use of a stylet. Such a stylet 410 is seen being displaced through a catheter 20 in FIGS. 17 and 17A. Apparatus associated with stylet 410 includes a proximal handle 412, a stylet attachment module 420 and a blunted end 430. Note that end 430 should be effectively blunted so that no catheter damage is caused while threading stylet 410 through catheter 20. Note, also, that end 430 is preferably recessed approximately one centimeter from distal end 100 when stylet 410 is fully inserted to assure stylet end 430 does not contact a blood vessel. While end 430 is shown as a spherical part, other shapes, as are well known and understood in the catheter art, may be used. As an example, stylet 410 and end 430 may be stainless steel.

Figures 18, 19:
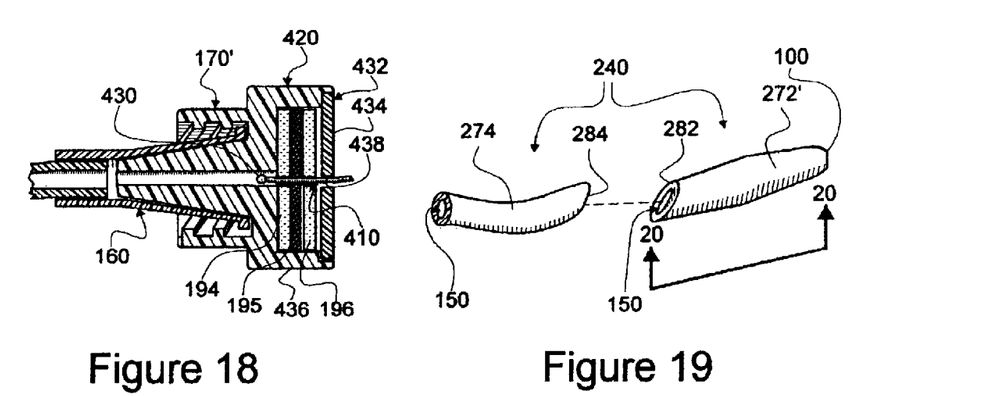
FIG. 18 is a cross section taken along lines 18—18 of FIG. 17.
FIG. 19 is a section, similar to the section seen in FIG. 7, of a catheter with a bulging distal portion.

Stylet attachment module 420 is better seen in cross section in FIG. 18. As seen in FIG. 18, module 420 is affixed to female luer fitting 160, with a male luer lock fitting 170'. Distally, module 420 is similar to vessel 50, however, module 420 is strictly shortened and blunted at a proximal end 432. At end 432, a cap 434 is securely affixed to a more distal, cylindrical body part 436 of fitting 170' to enclose pads which restrict proximal liquid flow and wipe a proximally displaced wire 410. The pads are preferably similar in form and function to pads, numbered 194, 195 and 196, used in fitting 170. Cap 434 has a medial hole 438 for passage of stylet 410.

Figure 17:
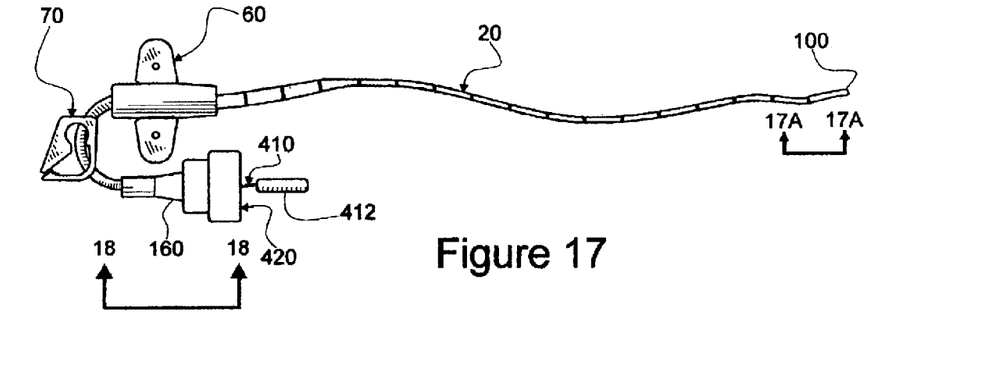
FIG. 17 is a top elevation of a midline catheter, similar to the catheter seen in FIG. 6, with a stylet disposed through the catheter.
Figure 17A:
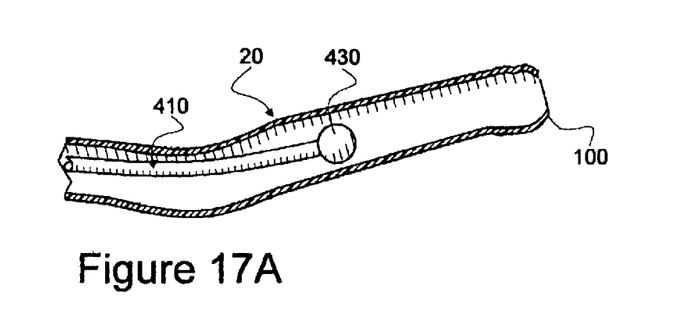
FIG. 17A is a section taken along lines 17A—17A of the midline catheter seen in FIG. 17.

When needed and provided, module 420 is affixed to luer fitting 160 by standard methods used in connecting catheter lines already attached to a patient and stylet 410 is threaded through catheter 20 until end 430 is distally disposed as seen in FIG. 17A to act as a guide for continued insertion of catheter 20.

In addition to a stylet, such as wire 410 and end 430, catheter insertion may be facilitated by providing a leading, distal portion, such as bulging portion 272' seen in FIG. 19. By providing such a bulging portion 272', in a distal tip section 240' of a midline catheter, it is possible to dilate contacted portions of a vessel and thereby more easily displace more pliant portions (reverse taper) of a catheter during catheter insertion.

Figure 20:
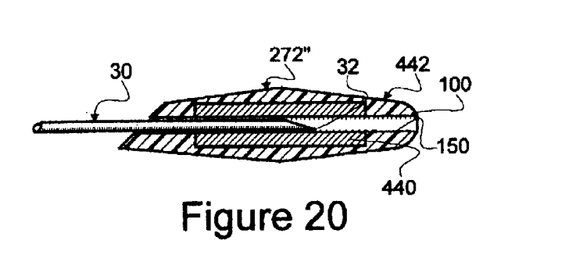
FIG. 20 is a cross section of the distal section portion, taken along lines 20—20 in FIG. 19.

Properly disposed, a needle cannula, such as cannula 30, may be employed to increase rigidity at distal end 100, as seen in FIG. 20. Note, in FIG. 20, that a distal portion 272", which is shaped similarly to distal portion 272' seen in FIG. 19, has a hollow, cylindrically shaped elongated insert 440 molded within body 442. To form portion 272", insert 440 may be placed upon a mandrel and body 442 thereafter molded about insert 440 to form portion 272". Insert 440 may be made from any of a number of biologically inert materials which are impervious to being pierced by sharpened end 32, which may include, but are not restricted to stainless steel, polypropylene and other synthetic resinous materials in common use in safety needle systems.

Figure 20A:
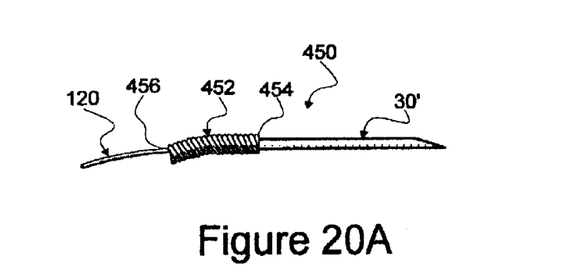
FIG. 20A is a side elevation of a medical needle cannula element having a spring affixed between a shortened needle cannula and a wire used to displace the needle cannula element.

It may be desirable to provide a needle cannula which is more pliant than a solid metal cannula like cannula 30. For this reason, a cannula/spring combination 450, as seen in FIG. 20A, may be employed in lieu of needle cannula 30. Combination 450 comprises a shortened cannula 30', relative to cannula 30, and a spring 452 affixed to cannula 30' on a distal end 454 and to wire 120 on a proximal end 456.

To use needle cannula 30, with safety to increase rigidity just proximal from end 100 of needle cannula 30, sharpened needle point 32 must be retracted and retained within insert 440. As distal displacement of wire 120 (and therefore needle cannula 30) is inhibited by geometry of vessel 200 relative to hole 198' (or by other methods and apparatus which impedes proximal displacement of wire 120, which is consistent with the present invention, see, for example, FIGS. 3 and 4), sharpened needle point 32 may be simply retracted a predetermined distance into insert 440.

Figure 21:
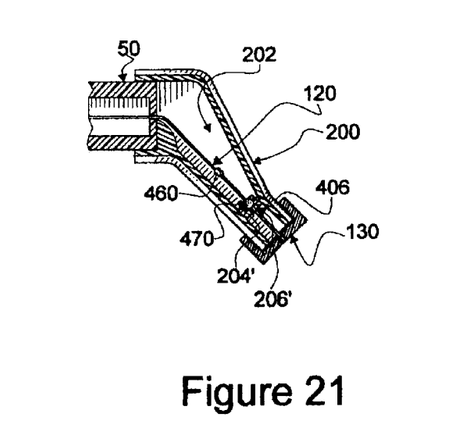
FIG. 21 is a cross section of a segment of a needle retraction housing and related other parts, which are similarly seen in FIG. 4, but wherein a wire retraction feature has been added.
Figure 22:
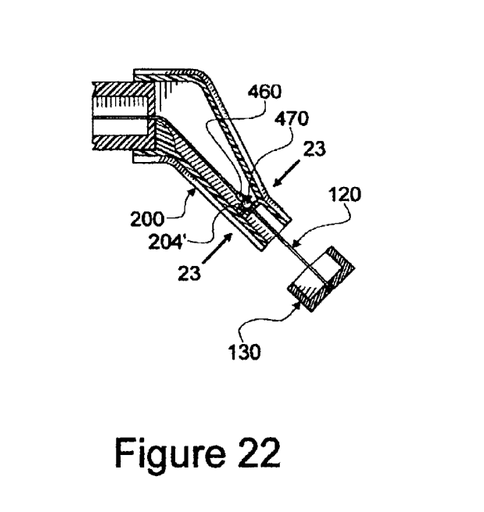
FIG. 22 is a cross section of a segment of a needle retraction housing and related other parts, similar to the section seen in FIG. 21, but wherein the wire retraction feature is in a retracted state.
Figure 23:
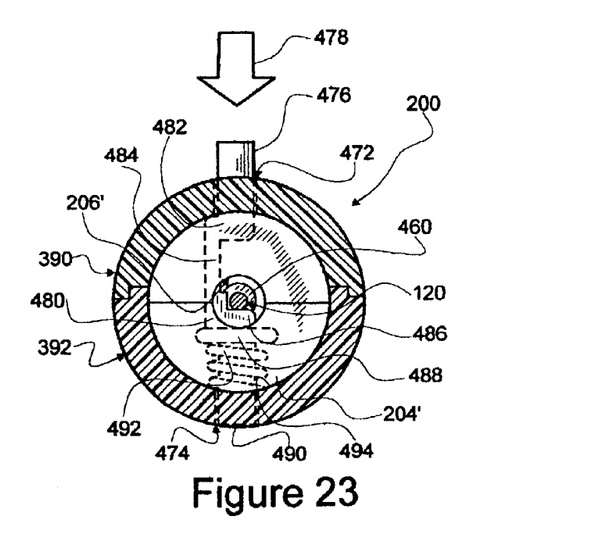
FIG. 23 is a cross section of the angled vessel seen in FIG. 22, taken along lines 23—23 of FIG. 22.

Such may be accomplished by affixing a mass to wire 120 as seen in FIGS. 21–23. As seen in FIG. 21, a mass 460, secured about wire 120, is displaced from a structural barrier 204' a distance which needle cannula 30 is pulled into portion 272' to fully enclose needle point 32 within insert 440 (see FIG. 20). As seen in FIG. 22, proximal displacement of cap 130, and therefore wire 120, is limited by an impediment or latch 470, which is distally disposed relative to barrier 204'. (Note that barrier 204' is similar in form to structure 204, seen in FIG. 2.)

As seen in FIG. 23, barrier 204' has a medially disposed hole 206' which is sized to pass wire 120 and mass 460. However, passage of mass 460 is blocked by latch 470. Latch 470 is slideably affixed to parts 390 and 392 of vessel 200 via juxtaposed, respective slots 472 and 474. Slot 472 is sized and shaped to permit a cylindrically shaped release pin 476 to be downwardly depressed in direction of arrow 478. Inferiorly disposed relative to pin 476, latch 470 comprises a frame 480 which is arcuately configured to include a shoulder 482, a thinned section 484, a stop 486, a bushing 488 and a guide pin 490. Note that slot 474 is sized and shaped to permit passage of guide pin 490. A compression spring 492 is captured about pin 490 between bushing 488 and an inner surface 494 of vessel 200. Being distally disposed relative to barrier 204', portions of latch 470 and spring 492 are represented by dashed lines seen in FIG. 23.

Latch 470 is facilely assembled into vessel 200 at the time part 390 is affixed to part 392. Spring 492 is fitted about guide pin 490 and guide pin 490 is inserted into slot 474. Similarly, pin 476 is inserted into slot 472.

Note in one state, as seen in FIG. 23, stop 486 of latch 470 blocks proximal displacement of wire 120 at a proximal end of mass 460. So disposed latch 470 effectively limits proximal travel of sharpened point 32 of needle cannula 30 to an incremental displacement as seen in FIG. 20. When it is desired to completely withdraw needle cannula 30 from catheter 20 into vessel 180, pin 476 is depressed and cap 130 is further proximally displaced. Depression of pin 476 displaces thinned section 484 into alignment with mass 460 permitting passage of mass 460 through hole 206' and, finally, extraction of wire 120 and cannula 20 from catheter 20.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. Safety midline catheter apparatus comprising:
    a catheter specifically intended for midline catheter applications, said catheter having a length, circumscribed about a hollow lumen of substantially constant internal diameter such that an increase in outside diameter of a portion of said catheter results in a consequential increase in catheter wall thickness, comprising a distal section, a medial section, and two proximal sections;
    said distal section having a predetermined outer diameter sized for over-the-needle skin insertion and being made of sufficiently rigid material for over-the-needle venipuncture;
    said medial section, proximally disposed relative to said distal section, also having the predetermined outer diameter and being made of a material which is pliable but which has sufficient stiffness to facilitate threading of the distal section of the catheter inserted at a venipuncture site and threaded to a predetermined target site;

said two proximal sections comprising a tapered section and a most proximal section which has an essentially constant diameter which is larger than the outer diameter of the distal and medial sections, said tapered section being disposed immediately proximally relative to said medial section and being tapered from the outer diameter of the medial section to an outer diameter which is the larger outer diameter of said most proximal section, whereby tapering of said tapered section, in conjunction with the internal diameter of the hollow lumen, provides a wall thickness which effectively resists kinking and associated closure of said lumen which might be associated with bending of the catheter such as may occur due bending of an elbow by a patient into which the catheter is inserted;

a hollow needle cannula disposed within said lumen and having a sharpened distal end which is exposed for catheter insertion;

an elongated wire affixed, at a distal end, to a proximal end of said needle cannula and, at a proximal end, to a fixture whereby the needle is proximally displaced after catheter insertion; and a safety needle enclosure apparatus into which the needle is displaced and secured, said safety enclosure apparatus comprising means for securely, but releasibly affixing said wire in place, for proximally displacing said hollow needle and for effectively resisting distal displacement of said elongated wire thereby assuring the needle and associated sharpened tip can only be displaced proximally.

2. Safety midline catheter apparatus according to claim 1 wherein said enclosure apparatus comprises a first hollow, elongated vessel which is of sufficient length to fully contain a needle cannula displaced therein, said vessel having a proximal hole sized to permit displacement of said wire but which retards passage of said needle cannula, said apparatus further comprising a second hollow, elongated vessel, affixed on a distal end to a proximal end of said first vessel, said second vessel comprising an angled pathway for said wire which, in combination with said proximal hole, effectively retards distal displacement of said wire thereby assuring unidirectional displacement of said needle cannula and retention of said needle cannula in said first vessel which is therefore a safety housing for said needle cannula.

3. Safety midline catheter apparatus according to claim 2 wherein said means comprise a cap which is securely affixed to said wire and which is releasibly affixed to a proximal end of said second elongated vessel.

4. Safety midline catheter apparatus according to claim 3 wherein said cap and said second elongated vessel, in combination, comprise a releasable latch whereby the cap is released from the second elongated vessel only by a quarter turn twist of said cap relative to said second elongated vessel thereby reducing likelihood of inadvertent proximal displacement of said wire and needle cannula.

5. Safety midline catheter apparatus according to claim 1 wherein said catheter comprises a window disposed along the length thereof which is sufficiently transparent to permit facile visualization of blood flash.

6. Safety midline catheter apparatus according to claim 1 wherein said enclosure apparatus comprises a liquid flow barrier proximal to the catheter such that blood flow is restricted to wire and needle cannula pathways which are distal to the safety housing.

7. Safety midline catheter apparatus according to claim 6 wherein said liquid flow barrier comprises material which permits venting air from the catheter to permit proximal blood flow through the catheter while said catheter is affixed to said enclosure apparatus.

8. Safety midline catheter apparatus according to claim 7 wherein said material is Gortex.

9. Safety midline catheter apparatus according to claim 7 wherein said liquid flow barrier comprises a foam material which wipes both said wire and said needle cannula being pulled through said foam material.

10. Safety midline catheter apparatus according to claim 7 wherein said liquid flow barrier is sufficiently elastic to close any opening and provide a barrier to liquid flow after said wire and said needle cannula are completely pulled therethrough.

11. Safety midline catheter apparatus according to claim 1 wherein said midline catheter comprises an elongated radiopaque strip along the wall of the catheter which permits fluoroscopic tracking of a pathway of the catheter after insertion.

12. Safety midline catheter apparatus according to claim 1 wherein said midline catheter comprises circumferential marks about the catheter spaced at predetermined intervals for the purpose of determining distance a catheter is inserted.

13. Safety midline catheter apparatus according to claim 1 wherein said midline catheter comprises an associated butterfly member by which the catheter is gripped for purposes of inserting both needle and catheter and otherwise for maintaining position control of the catheter during use, the butterfly being displaceable along the catheter, having a slit collet disposed about the catheter and being formed of material which is sufficiently flexible to permit opening of the slit in the collet to permit disengagement of the catheter from the collet of the butterfly while the butterfly is resident upon a skin surface of a patient.

14. Safety midline catheter apparatus according to claim 1 wherein said midline catheter distal section comprises a most distal end, designed for over-the needle catheter insertion, which has sufficient rigidity for over-the-needle insertion.

15. Safety midline catheter apparatus according to claim 1 wherein said midline catheter medial section comprises a material which is more supple than the distal section, but has sufficient rigidity for threading the distal section to a predetermined target site and which has a first outer diameter which is the same outer diameter of the distal section.

16. Safety midline catheter apparatus according to claim 1 wherein said midline catheter tapered section is disposed at a site along the catheter such that the smaller diameter portion of an inserted catheter is displaced beyond the antecubital crease and the tapered section and larger diameter section are ordinarily disposed in the region of the antecubital crease when said catheter is used in midline catheter applications.

17. Safety midline catheter apparatus according to claim 1 wherein said distal section comprises an exterior circumferential bulging portion which is greater than the predetermined outer diameter, said bulging portion providing an enlarged distal segment which facilitates threading said midline catheter through anatomical pathways of a blood vessel.

18. Safety midline catheter apparatus according to claim 17 wherein said distal segment houses a safety insert which protects from inadvertent trauma which otherwise might be delivered by a sharpened point disposed for protection therein.

19. Safety midline catheter apparatus according to claim 18 wherein said safety needle enclosure apparatus further comprises a latch which limits withdrawal of said needle cannula such that the sharpened distal end is disposed within the insert when said wire is first proximally displaced.

20. Safety midline catheter apparatus according to claim 19 wherein said latch comprises a release whereby said needle cannula is freed to be completely withdrawn into said safety enclosure apparatus.

21. Safety midline catheter apparatus according to claim 1 wherein said apparatus further comprises a stylet which is selectively used to stiffen the midline catheter.

22. Safety midline catheter apparatus according to claim 21 where said stylet comprises a length which, when fully inserted, avoids protrusion beyond the distal end of the catheter, thereby avoiding any contact with a vessel exterior to said catheter.

23. A midline catheter comprising:

a catheter specifically intended for midline catheter applications, said catheter having a length, circumscribed about a hollow lumen of substantially constant internal diameter such that an increase in outside diameter of a portion of said catheter results in a consequential increase in catheter wall thickness, comprising a distal section, a medial section, and two proximal sections;

said distal section having a predetermined outer diameter sized for over-the-needle venipuncture and being made of sufficiently rigid material for over-the-needle venipuncture;

said medial section, proximally disposed relative to said distal section, also having the predetermined outer diameter and being made of a material which is pliable but which has sufficient stiffness to facilitate threading of the distal section of the catheter from a point of insertion at site near the antecubital crease and threaded to a predetermined target site;

said two proximal sections comprising a tapered section and a most proximal section having an essentially constant outer diameter which is larger than the outer diameter of the distal and medial sections, said tapered section being disposed immediately proximally relative to said medial section and being tapered from the outer diameter of the medial section to an outer diameter which is the larger outer diameter of said most proximal section, whereby tapering of said tapered section, in conjunction with the internal diameter of the hollow lumen, provides a wall thickness which effectively resists kinking and associated closure of said lumen which might be associated with bending of an elbow by a patient into which the catheter is inserted;

an associated butterfly member by which the catheter is gripped for purposes of inserting both needle and catheter and otherwise for maintaining position control of the catheter during use, the butterfly being displaceable along the catheter, having a slit collet disposed about the catheter and being formed of material which is sufficiently flexible to permit opening of the slit in the collet to permit disengagement of the catheter from the collet of the butterfly while the butterfly is resident upon a skin surface of a patient.

* * * * *